United States Patent
Blythe et al.

(10) Patent No.: US 10,605,759 B2
(45) Date of Patent: Mar. 31, 2020

(54) VERIFYING OPERATION OF A METER (71) Applicant: INSIDE BIOMETRICS LIMITED, Dingwall (GB)

(72) Inventors: Stephen Blythe, Dingwall (GB); Damian Baskeyfield, Dingwall (GB)

(73) Assignee: INSIDE BIOMETRICS INTERNATIONAL LIMITED, Dingwall (GB)

( * ) Notice: Subject to any disclaimer, the term of this patent is extended or adjusted under 35 U.S.C. 154(b) by 70 days.

(21) Appl. No.: 15/531,077

(22) PCT Filed: Nov. 26, 2015

(86) PCT No.: PCT/GB2015/053602
§ 371 (c)(1),
(2) Date: May 26, 2017

(87) PCT Pub. No.: WO2016/083810
PCT Pub. Date: Jun. 2, 2016

(65) Prior Publication Data
US 2018/0172618 A1    Jun. 21, 2018

(30) Foreign Application Priority Data
Nov. 26, 2014  (GB) .................................. 1420982.9

(51) Int. Cl.
*G01N 27/416* (2006.01)
*G01N 27/327* (2006.01)
*G01N 33/487* (2006.01)

(52) U.S. Cl.
CPC ... *G01N 27/3274* (2013.01); *G01N 33/48785* (2013.01)

(58) Field of Classification Search
CPC .................... G01N 27/3274; G01N 33/48785
See application file for complete search history.

(56) References Cited

U.S. PATENT DOCUMENTS 5,124,661 A    6/1992  Zelin et al.
5,438,271 A *  8/1995  White ................ G01N 27/3273
                                                 204/406

(Continued)

FOREIGN PATENT DOCUMENTS

| DE | 4318891 A1 | 12/1994 |
| EP | 2042865 A2 | 4/2009 |
| GB | 2511345 A | 9/2014 |

OTHER PUBLICATIONS

International Search Report and Written Opinion issued in PCT/GB2015/053602 dated Feb. 3, 2016.

(Continued)

*Primary Examiner* — J. Christopher Ball
(74) *Attorney, Agent, or Firm* — Tarolli, Sundheim, Covell & Tummino LLP (57) ABSTRACT

A method of verifying operation of a meter for reading electrochemical test devices, includes obtaining a reference output signal indicative of a response generated at an electrochemical test device when the electrochemical test device reacts with a reference test fluid; applying with the meter an algorithm to the reference output signal so as to obtain a reference test result, wherein the algorithm is for use in estimating an unknown concentration of an analyte in a sample of the reference test fluid; and determining whether the reference test result is valid so as to verify operation of the meter.

15 Claims, 6 Drawing Sheets (56) References Cited

U.S. PATENT DOCUMENTS

| | | | |
|---|---|---|---|
| 5,781,024 A | 7/1998 | Blomberg et al. | |
| 2004/0200720 A1* | 10/2004 | Musho | C12Q 1/001 |
| | | | 204/403.01 |
| 2006/0163086 A1* | 7/2006 | Bae | G01N 27/3273 |
| | | | 205/775 |
| 2009/0194432 A1 | 8/2009 | Deng | |
| 2011/0294152 A1* | 12/2011 | Lipman | G16H 40/63 |
| | | | 435/29 |

OTHER PUBLICATIONS

Search Report issued in Great Britain Patent Application No. 1420982.9 dated May 21, 2015.

\* cited by examiner

VERIFYING OPERATION OF A METER

FIELD OF THE INNOVATION

The present disclosure relates to a method of verifying operation of a meter for reading electrochemical test devices. In specific embodiments the test device is an electrochemical test strip as used with bodily fluid meters for determining the concentration of analytes in an individual's bodily fluid sample.

BACKGROUND

In the field of diagnostic and monitoring devices as used in the medical device industry, especially those used for analysing blood or other bodily fluid samples, it is often required for users to monitor biometrics such as the levels of certain chemicals, substances, or analytes present in their bloodstream. For instance, diabetics in particular must regularly monitor the concentrations of glucose in their blood in order to determine if they are in need of insulin. In order to respond effectively to an individual's needs to monitor blood sugar levels, diagnostic and monitoring devices and kits have been developed over the years to allow an individual to autonomously determine the concentration of glucose in their bloodstream, in order to better anticipate the onset of hyperglycaemia or hypoglycaemia and take preventative action as necessary. The existence of such diagnostic and monitoring devices places less strain on the healthcare system at large, as patients are able to administer insulin in their own home and without having to do so in the presence of a medical professional.

Typically the patient will, using a lancing device, perform a finger stick to extract a small drop of blood from a finger or alternative site. An electrochemical test device, which is often a strip, is then inserted into a diagnostic/monitoring meter, and the sample is applied on the test strip. Through capillary action, the sample flows across a measurement chamber of the device and into contact with one or more electrodes or similar conductive elements coated with sensing chemistry for interacting with a particular analyte or other specific chemical (for example glucose) in the blood sample. The magnitude of the reaction is dependent on the concentration of the analyte in the blood sample. The meter may detect the current generated by the reaction of the reagent with the analyte, and the result can be displayed to the user.

It is important that the reading output by a meter can be relied upon so that if necessary appropriate action may be taken. If the reading is erroneous and the user acts upon the erroneous reading, any action taken (e.g. the administration of insulin) could be detrimental to the user's health. Erroneous readings can arise not only if the test strip is damaged (which could for example affect the flow of the fluid sample across the measurement chamber), but also if the meter itself is damaged.

To address this issue, control solutions having known concentrations of one or more analytes have been developed. The control solution is applied to a test strip and tested using the meter, usually when a new batch of strips is opened. Because the concentration of the analyte of interest in the control solution is known, the meter reading is expected to fall within a predetermined range (usually indicated on the vial containing the strips). If the reading passes this test then the user is given the confidence to proceed with a blood-analyte measurement. As an increased precaution, governmental regulatory bodies such as the FDA generally require that in order to be fit for distribution a meter must satisfy a test of multiple control solutions with different concentrations of analyte. Control solutions are important and useful for verifying the integrity of one or more strips as well as the calibration of the meter itself. However, unless a relatively simple measurement/algorithm is used with the control solution (e.g. a single current reading at a fixed time, and a slope and intercept to convert the current value to an analyte reading), control solutions generally do not allow for verification of the integrity of the meter hardware and software responsible for carrying out an analyte measurement when a non-control solution is being tested. Whilst this could be addressed by developing control solutions that mimic the behaviour of blood (or whatever non-control solution is being tested), such development could not be arrived at without significant time and expense given that blood is a complex matrix sample containing many constituents not present in simple control solutions (such as blood cells).

There therefore remains a need in the art to carry out a check of the meter components responsible for carrying out an analyte measurement when a non-control solution (e.g. blood) is being tested, without having to develop blood-mimicking control solutions. The present disclosure seeks to address this need.

SUMMARY OF THE DISCLOSURE

In accordance with a first aspect, there is provided a method of verifying operation of a meter for reading electrochemical test devices. The method comprises obtaining a reference output signal indicative of a response generated at an electrochemical test device when the electrochemical test device reacts with a reference test fluid. The method further comprises applying with the meter an algorithm to the reference output signal so as to obtain a reference test result. The algorithm is for use in estimating an unknown concentration of an analyte in a sample of the reference test fluid. The method further comprises determining whether the reference test result is valid so as to verify operation of the meter.

The reference output signal (which may be referred to in the art as a reference transient) may be obtained through various means. For example, the reference output signal may be pre-stored in the meter, for example during manufacturing of the meter. Alternatively, the reference output signal may be obtained immediately prior to verification of the meter operation, and may be provided to the meter wirelessly or via a mass storage device or similar device.

The reference output signal may be indicative or representative of a response, such as a current vs time response, generated at an electrochemical test device when the electrochemical test device reacts with a reference test fluid (e.g. a non-control fluid). The reference output signal does not have to represent an actual real response measured at a test device, but instead may be representative or indicative of multiple measured responses, in which case the reference output signal may be an average of the measured responses. The reference output signal may therefore be indicative or representative of a response from a predefined reference test fluid under certain conditions (e.g. temperature).

The reference output signal may be obtained from a reference test fluid having known parameters, for example known haematocrit (in the case of blood), known temperature, and known or average endogenous or exogenous interfering substances. Other parameters fall within the scope of this disclosure. Thus, a reference output signal or transient may be obtained from a sample of reference test fluid having known parameters, and the transient may then be stored in the meter for later use. The reference output signal or transient may therefore represent a typical transient or response that would be generated at a test device using a sample of the reference test fluid in question. More than one reference transient may be stored or otherwise obtained, in particular depending on the number of working electrodes present on the test device. In addition, other parameters may be determined by the meter and used in selecting an appropriate reference transient. For example, the meter may be arranged to determine a temperature of a fluid sample applied to a test strip inserted within the meter, for example through the use of thermistors. A temperature reading could then be used to assist the meter in determining which reference transient to use for carrying out the above-described system check.

The algorithm may be any algorithm designed or arranged for estimating a concentration of an analyte in a sample of the reference test fluid. The algorithm may be suitable for being applied to a response transient comprising multiple time points, that is an algorithm arranged to operate on multiple points of a test transient obtained by the meter. Examples of such algorithms are disclosed in co-pending UK application 1419799.0, which is incorporated herein by reference.

The reference test result obtained from the application of the algorithm to the reference output signal may be a reading of a concentration of the analyte representative of the reference fluid sample, or may be some other reading such as a current or other electrical characteristic. The reference test result may also comprise any other characteristic or feature resulting from the application of the algorithm to the reference output signal. The meter may read the reference transient and algorithm code and apply the algorithm to the reference transient. This may provide a suitable reference analyte reading which may be checked internally in the meter against expected results with an allowable tolerance. If the simulated reading is out of the allowable tolerance, the meter will give a suitable error message and ask for a re-test, and may not display the meter reading for the real transient. In some embodiments, the system check may occur after the collection of the real transient. In other embodiment, the system check may occur before the collection of the real transient.

Advantageously, by using a reference transient indicative of a response generated using a non-control (reference) test fluid, and by applying an algorithm designed for use in estimating a concentration of an analyte in a sample of the reference test fluid, the contemplated embodiments allow a user to carry out an integrity check of the algorithm used for measuring concentrations of analytes in test fluids. The described embodiments therefore allow for a more complete system check of the meter as a whole, by testing the part of the system responsible for the blood-analyte measurement (or more generally the test fluid—analyte measurement). The described embodiments provide a further system check for ensuring proper functioning and performance of the meter, and better safeguards the safety of users.

The reference output signal may be stored in a memory of the meter. The memory may be non-volatile or volatile memory. Because the reference transient may be read from a memory, the integrity of the memory is also checked, providing a wider check of the system.

An anomaly in the reference output signal may be identified in response to determining the reference test result is not valid. If the reference test result is not valid, for example if the simulated reading obtained from applying the algorithm to the reference transient is not within an expected range, then it may be determined that the reference transient is corrupted, and one or more anomalies within the stored reference transient may be detected. In the case where the reference transient is stored in a non-volatile memory of the meter, an anomaly in the reference transient may correspond to corruption of a portion of the non-volatile memory responsible for storing the anomalous portion of the reference transient. If additional memory capacity is available, the damaged portion of memory could in future be avoided to enable continued proper functioning of the meter.

An error in the algorithm may be identified in response to determining the reference test result is not valid. Thus, the error in the algorithm may correspond to a corruption of a (non-volatile or volatile) memory of the meter storing the algorithm. More generally, a corruption of a memory of the meter may be determined, the memory storing the reference output signal and/or the algorithm.

The reference test fluid sample may be a bodily fluid sample selected from the following: blood, plasma, urine, saliva, lacrimal fluid, sweat, and interstitial fluid; or breath condensate.

The reference output signal may be obtained from multiple output signals generated using respective samples of the reference test fluid, each sample obtained from a member of a common demographic. For example, the reference output signal or transient may be an average of a multiple 'real' output signals or transients generated using respective samples of the reference test fluid. The demographic may comprise a person whose test fluid is being tested. For example, when testing a blood sample of a diabetic, a reference output signal obtained from a diabetic may be used when verifying operation of the meter. The common demographic may comprise any of the following: diabetics (including Types 1&2, and Gestational), non-diabetics, males, females, adults, children, persons within a specific age range, persons taking a particular medication, etc.

The analyte may be any of the following: glucose, ketone, lactate, glycerol and cholesterol. As would be understood by the skilled person, other analytes fall within the scope of the disclosure.

The reference output signal may be obtained from multiple output signals generated using respective samples of the reference test fluid, each sample having substantially the same temperature.

The method may further comprise applying a control fluid to an electrochemical test device; obtaining with the meter a control output signal indicative of a response generated at the electrochemical test device when reacting with the control fluid; and verifying operation of the meter based on the control output signal. Thus, in combination with the algorithm/hardware check, a check of the electrochemical test device may also be carried out. The meter may contain calibration information for the control solution for a particular analyte, usually in the form of a simple relationship between the concentration of the analyte in the control solution and the meter reading (e.g. a straight line or a sigmoidal function). By generating a meter reading using the control solution on a strip, in addition to running a reference transient through the algorithm (as described above), a full system check may be carried out, without the need for major control solution development.

Verifying operation of the meter based on the control output signal may comprise: using a current generated at the electrochemical test device when reacting with the control fluid to estimate a concentration of an analyte in the control fluid; and comparing the estimated concentration to a predetermined range of concentrations. The control fluid may have a known concentration of the analyte.

The reference output signal may be pre-stored in a volatile or non-volatile memory of the meter before applying the control fluid.

In a second aspect, there is provided a meter for reading electrochemical test devices. The meter comprises one or more memories storing a reference output signal indicative of a response generated at an electrochemical test device when the electrochemical test device reacts with a reference test fluid.

The one or more memories further comprise an algorithm for use in estimating an unknown concentration of an analyte in a sample of the reference test fluid. The meter further comprises a processor configured to apply the algorithm to the reference output signal so as to obtain a reference test result. The processor is further configured to determine whether the reference test result is valid so as to verify operation of the meter.

BRIEF DESCRIPTION OF THE DRAWINGS

Specific embodiments will now be described in connection with the accompanying drawings, of which.

DETAILED DESCRIPTION

The present disclosure seeks to provide an improved method of verifying operation of a meter. Whilst various embodiments are described below, the contemplated embodiments are not limited to these embodiments, and variations of these embodiments may well fall within the scope of the appended claims.

Figure 1:
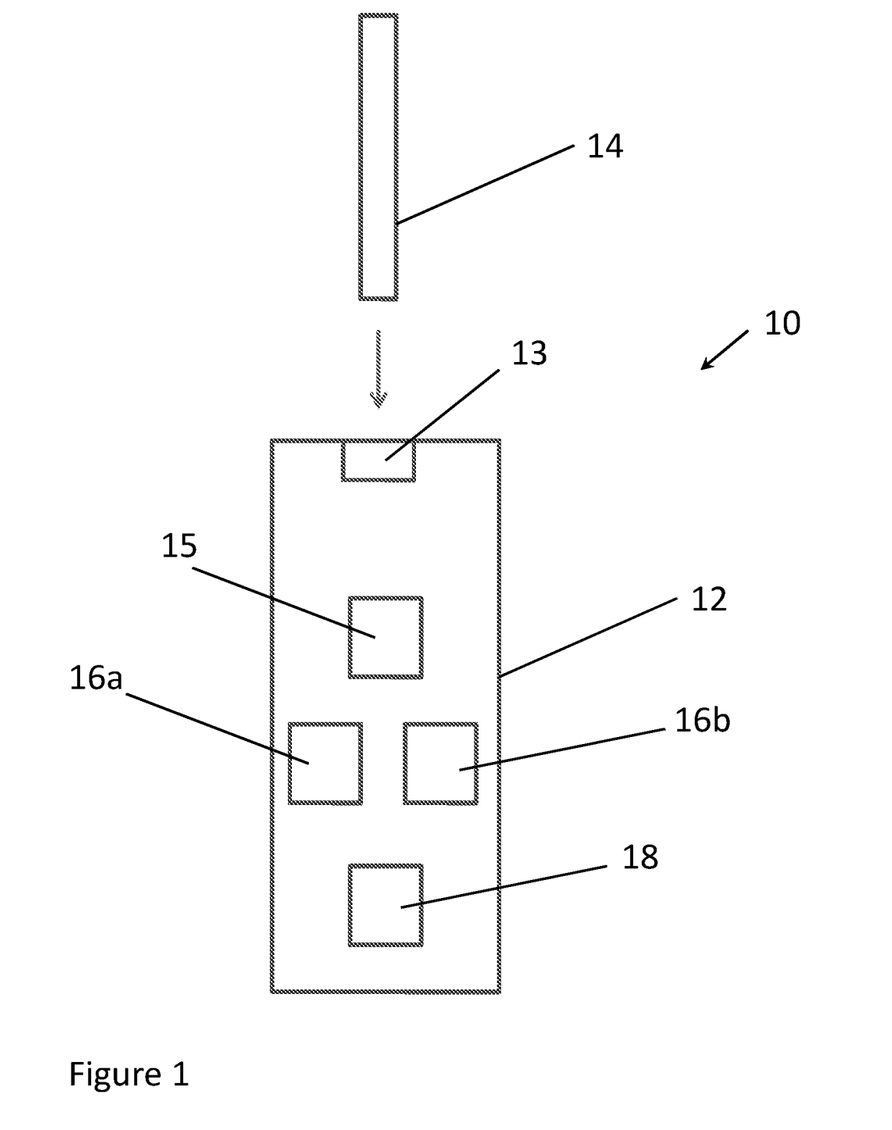
FIG. 1 is a schematic representation of a meter arranged to read an electrochemical test strip, in accordance with an embodiment.

FIG. 1 shows a strip-meter system 10 according to an embodiment. System 10 comprises a meter 12 for reading an electrochemical test strip 14. Electrochemical test strip 14 comprises one or more working electrode (not shown) and a counter/reference electrode, each of the working electrodes having a reagent coated thereon for reacting with a fluid sample to be applied to electrochemical test strip 14. The counter/reference electrode may also have a reagent coated thereon. Meter 12 comprises receiving means 13 for receiving test strip 14 and applying a potential difference between the working electrode(s) and the counter/reference electrode.

Meter 12 further comprises processing circuitry 15 for carrying various functions relating to the operation of meter 12. For example, processing circuitry 15: controls operation of receiving means 13 so to control application of a potential difference between the working electrode(s) and the counter/ reference electrode; processes transients generated at test strip 14; controls the display of messages on display 18; etc.

Meter 12 further comprises first and second memory storages 16a and 16b. Although two memory storages are shown, in other embodiments the memory storages may be combined to form a single memory storage, or meter 12 may comprise more than two memory storages. Meter 12 also comprises a display 18 for displaying readouts of measurements taken by meter 12.

Figure 2:
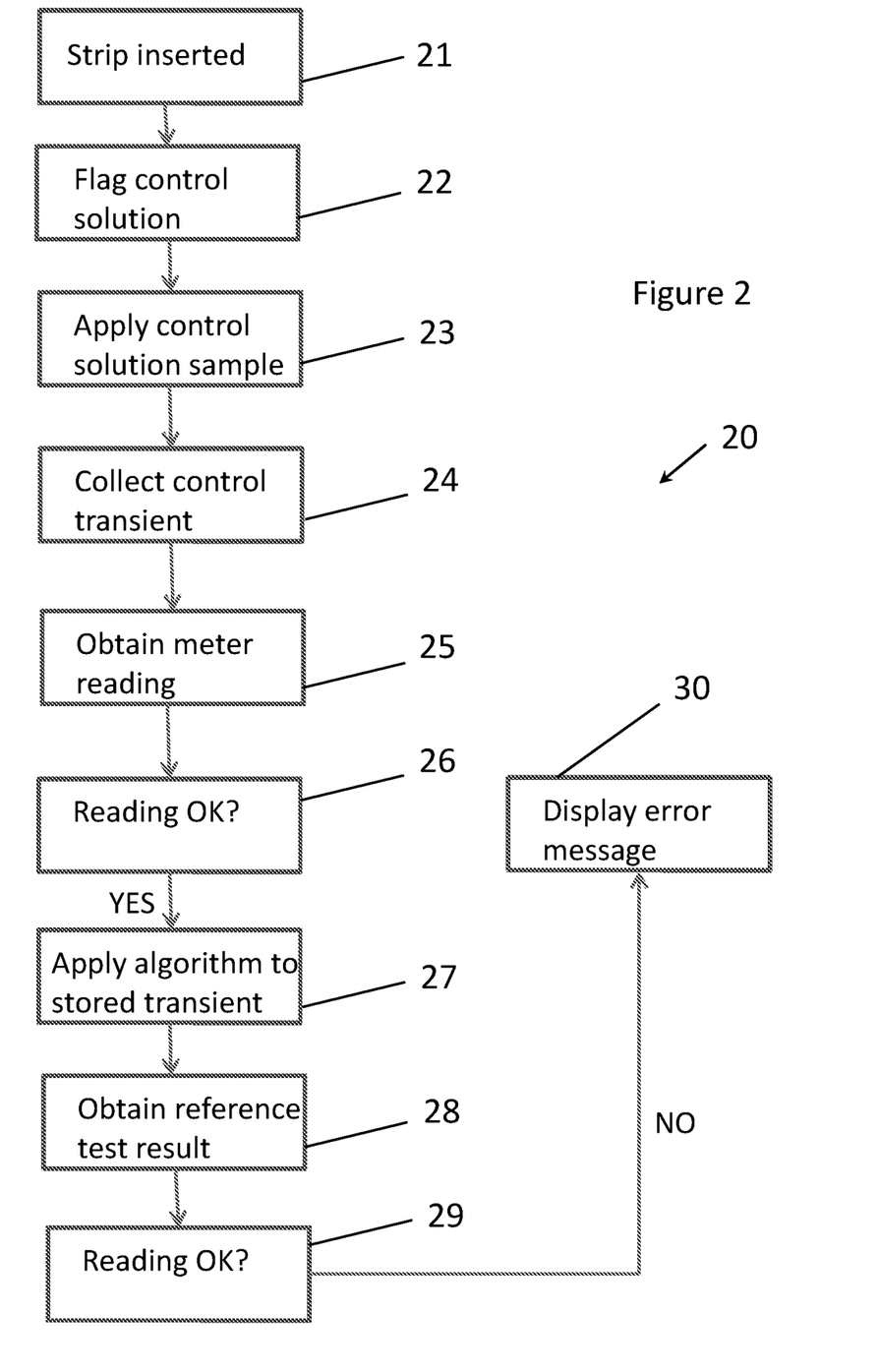
FIG. 2 shows a method of verifying operation of a meter for reading electrochemical test strips, in accordance with an embodiment.

A method 20 of verifying operation of meter 12 will now be described in connection with an embodiment. It should be noted that FIG. 2 shows an example method, and the order of the steps may be changed (for example the point in time at which the strip is inserted in the meter) without departing from the scope of the contemplated embodiments. The method may also comprise a fewer or greater number of steps.

Method 20 may be carried out for example when a user wishes to verify a new batch of strips, to ensure that the batch is not compromised because of manufacturing defects. At step 21, electrochemical test strip 14 is inserted within receiving means 13 of meter 12, in a reading position. In the reading position, receiving means 13 is positioned relative to the working electrode(s) of strip 14 so as to be able to apply a potential difference across the working electrode(s) and the counter/reference electrode, as known in the art. At step 22, the user provides input to meter 12 (for example via a control pad or similar user interface) to indicate to meter 12 that a control solution is to be tested. In an alternative embodiment, meter 12 may be arranged to automatically determine that the fluid sample applied to test strip 14 is a control solution, in which case step 23 would occur before step 22. Receiving means 13, under control of processor 15, then applies a potential difference across the working electrode(s) and the counter-reference electrode.

Figure 3:
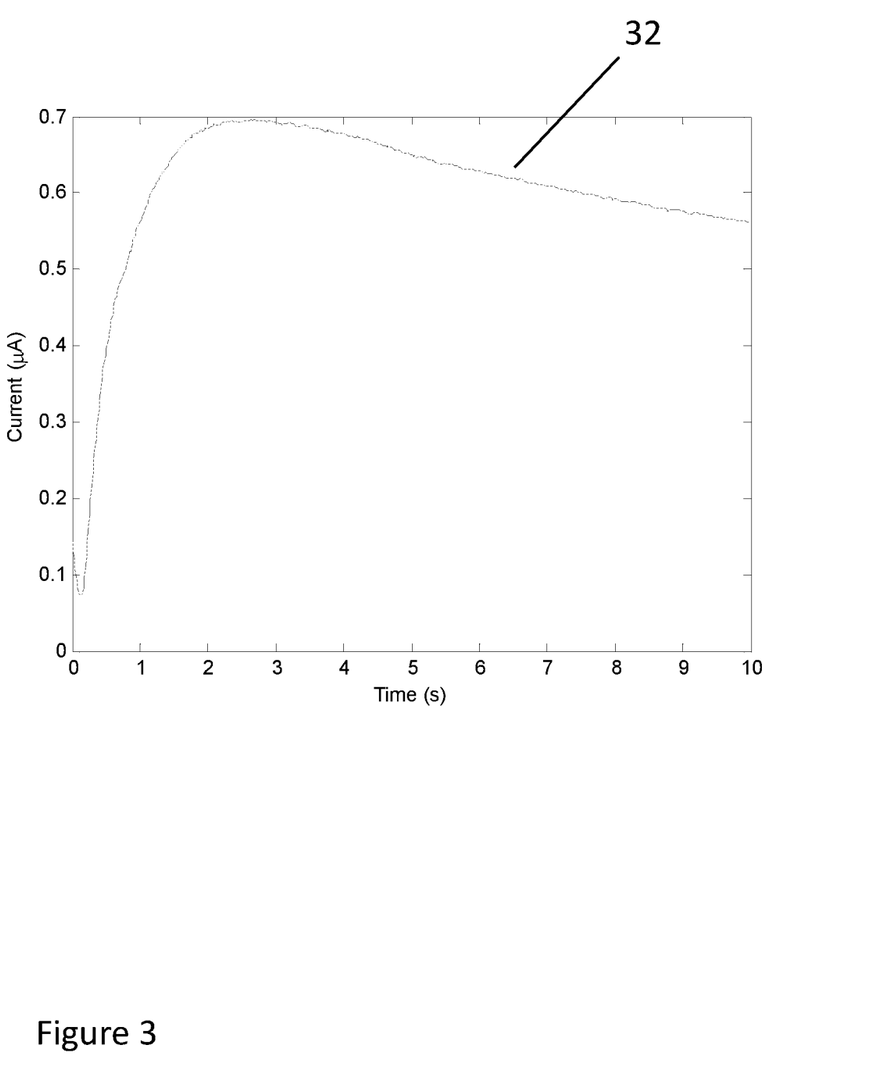
FIG. 3 shows a control transient obtained using a control solution.

At step 23, a sample of the control solution is applied to test strip 14. As known in the art, the control solution sample flows into contact with the working electrode(s) of strip 14 and reacts with the reagent coating the working electrode(s). The strength of the reaction depends on the concentration of analyte (e.g. glucose) within the control solution sample. At step 24, a control transient is collected and stored in memory storage 16a. The control transient is indicative or representative of the current vs time response generated at a working electrode and measured by meter 12. An example control transient is shown in FIG. 3. At step 25, a meter reading of the control transient is obtained. This is carried out by processor 18 applying a calibration code (stored in memory storage 16a) to the control transient. The calibration code is determined according to the user input provided to meter 12 at step 22. However, in other embodiments the calibration code may be fixed/hard-coded in meter 12 (for example if the manufacturing of strip batches is relatively consistent), or else may be auto-read for example from test strip 14. This will depend on the type of meter 12 that is used. The meter reading is taken at a predetermined time point (e.g. 10 seconds from when a current is first detected, or more preferably less than approximately 5 seconds from when a current is first detected) to determine the quantity of glucose within the control solution sample.

Turning to FIG. 3, we see a current vs time transient 32 generated by a sample of control solution. In this case the calibration code is applied at the final current (0.5608 µAmperes), measured at 10 seconds, and is used to make a measurement of the glucose concentration in the control solution sample. Applying the calibration entered into the meter with an intercept a=0.001 µA and a slope b=0.2 µA/mmol/L, the analyte concentration is determined to be C=(0.5608−0.001)/0.2=2.7989 mmol/L. The result is typically rounded to one decimal place to give C=2.8 mmol/L.

At step 26, the result is then verified against a range of acceptable concentrations, usually obtained by the user from the vial containing the test strips. If the reading is determined to be acceptable, then this confirms the integrity of test strip 14 as well as the integrity of memory storage 16a storing the control transient and calibration code.

Figure 4:
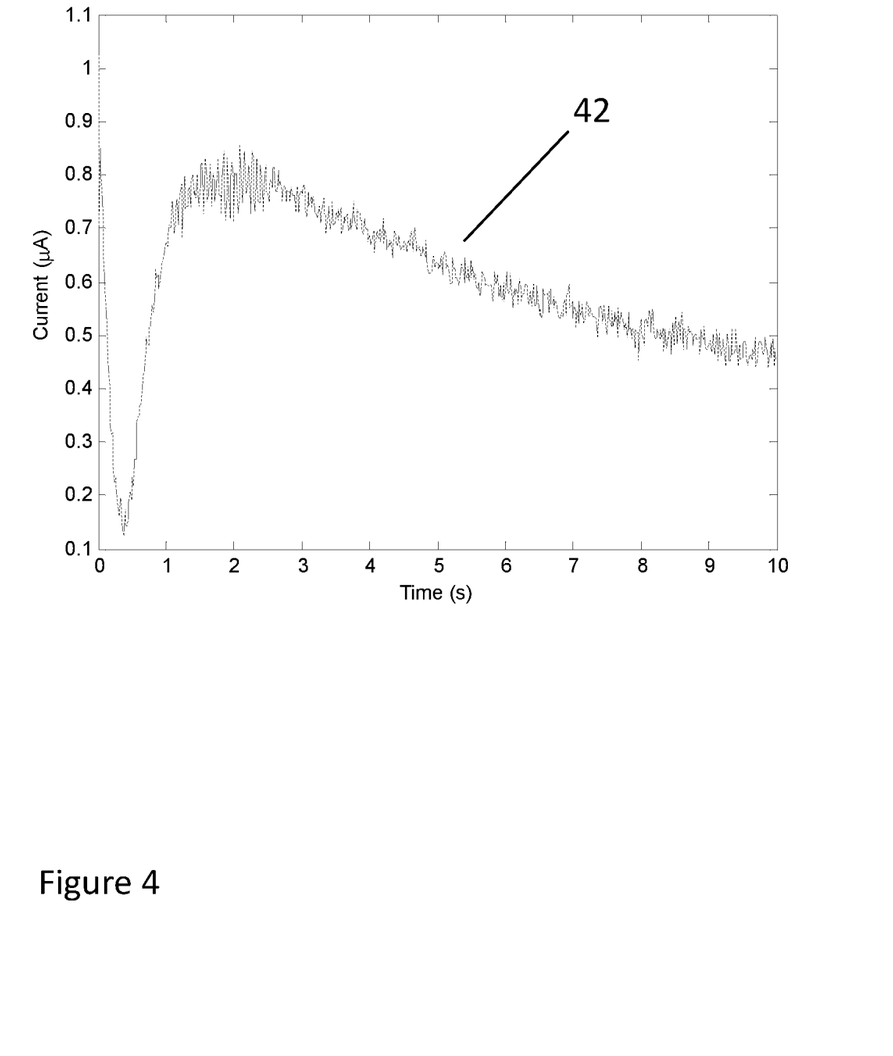
FIG. 4 shows a control transient obtained using a control solution, contaminated with noise

Now turning to FIG. 4, there is shown another control solution transient 42 where noise has contaminated transient 42. The end current in this case is 0.4523 µA, and thus, applying the calibration code stored in memory storage 16a, processor 18 would calculate an analyte concentration of C=(0.57−0.001)/0.2=2.2582 mmol/L, rounded to 2.3 mmol/L. In this case such a concentration is outside the expected range, so the user would detect a problem. This could be due to test strip 14, as in this case. In other embodiments, the erroneous reading could be due to a corruption of memory storage 16a storing the calibration code and the control transient.

The above control solution check represents a first test of meter-strip system 10. In particular, steps 22-26 represent a check of the integrity of test strip 14. Starting at step 27, a second check is carried out to determine whether the algorithm stored in memory storage 16b is functioning properly, i.e. if memory storage 16b is not corrupted. In some embodiments this check may be carried out whether or not the control solution check is carried out, or may be carried out before the control solution check.

Figure 5:
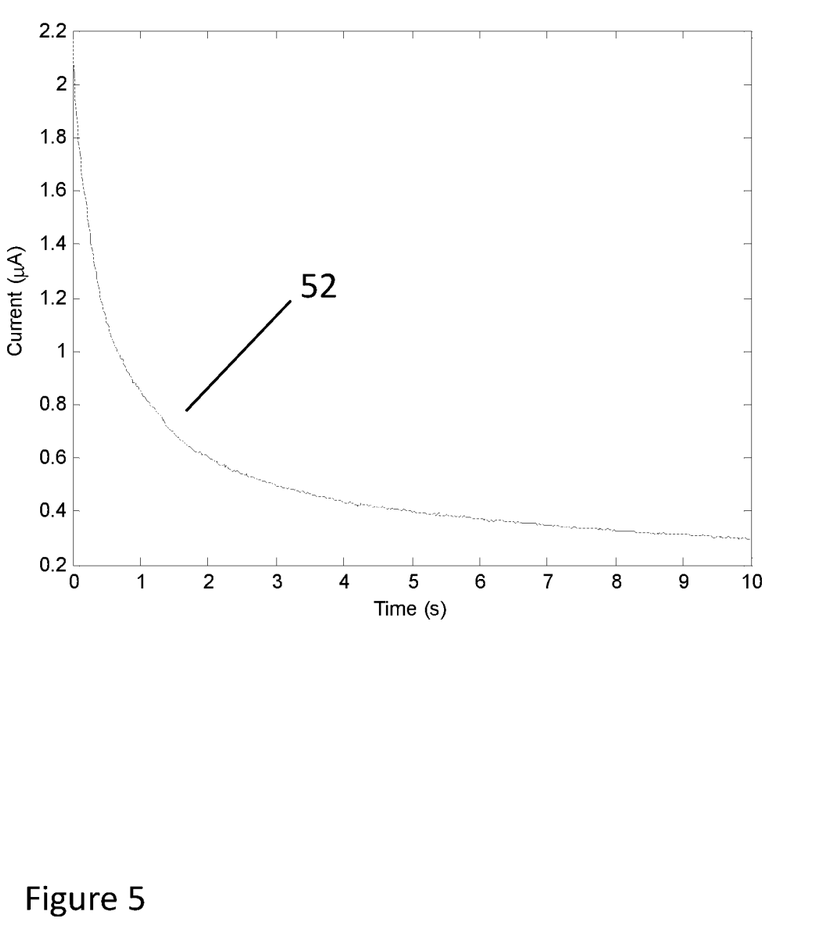
FIG. 5 shows a reference transient indicative of a current response generated at an electrochemical test strip.

Meter 12 comprises in memory storage 16b a pre-stored reference transient. An example reference transient 52 is shown in FIG. 5. The reference transient is representative or indicative of a current response generated at a particular working electrode given nominal blood conditions (e.g. known haematocrit, known temperature, etc.). The reference transient may have been obtained from a test of a real blood sample, or may be an average of multiple transients obtained from multiple samples of multiple members of a particular demographic.

Memory storage 16b may store more than a single reference transient, and for example may store one transient per working electrode of the test strip to be tested. For example, if test strip 14 includes a first working electrode with a specific reagent for reaction with analyte A, and a second working electrode with a specific reagent for reacting with analyte B, then memory storage 16b may include a first pre-stored reference transient for the first working electrode and a second pre-stored reference transient for the second working electrode. Depending on the working electrode triggered using control solution, processor 18 may know which stored reference transient to invoke. In other embodiments the particular control solution (e.g. containing a specific analyte and concentration thereof) that is applied and flagged/auto-detected by meter 12 will give rise to a response at the relevant working electrode. A single control solution may also be formulated for combined analytes (e.g. glucose and ketone). Note that the shape of reference transient 52 in FIG. 5 is different to that of the control transient in FIG. 3, as blood is more complex than control solution and includes various constituents (e.g. red blood cells white blood cells, proteins, hormones, antibodies, analytes and by-products) not present in control solution.

At step 27, processor 18 reads the reference transient stored in memory storage 16b and applies to the reference transient a blood-glucose algorithm also stored in memory storage 16b. The blood-glucose algorithm is arranged to estimate a concentration of glucose within a sample of blood. It will be apparent to a person skilled in the art that the algorithm may be arranged to determine a concentration of any analyte in any fluid sample, and is not limited to a blood-glucose algorithm.

Figure 6:
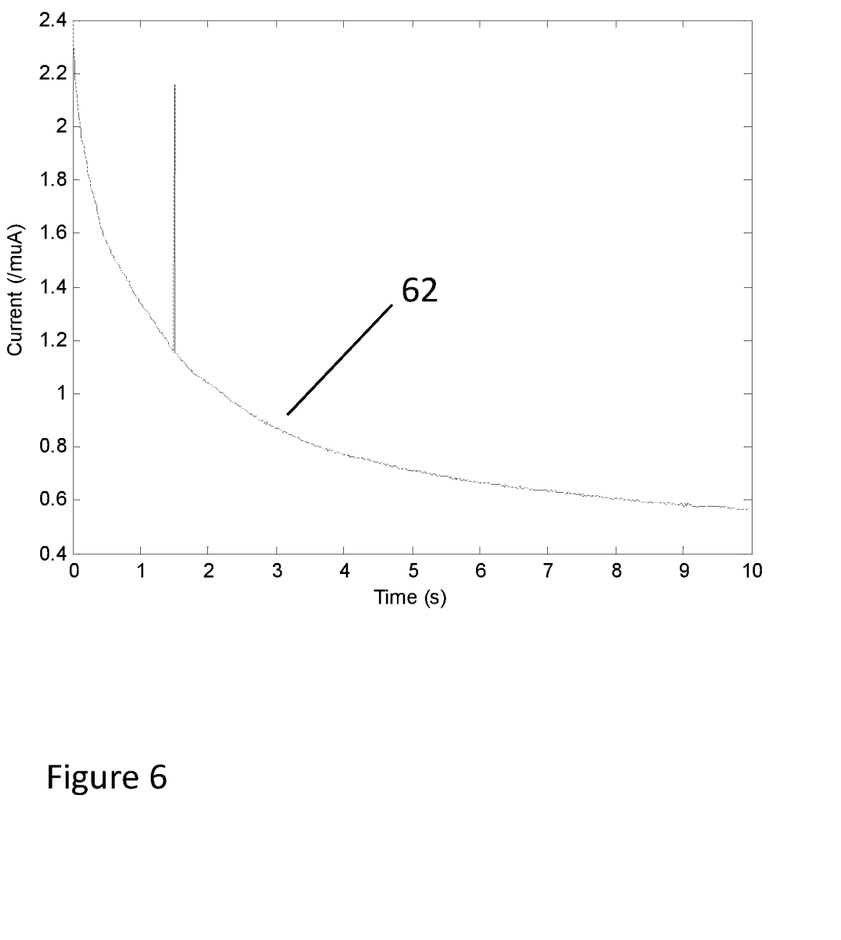
FIG. 6 shows a reference transient indicative of a current response generated at an electrochemical test strip, containing an anomaly.

If memory storage 16b is corrupted, then the reference transient will include a spike, dip, discontinuity, or similar artefact indicative of an error in memory storage 16b. An example of this is shown in reference transient 62 of FIG. 6. If the reference transient is corrupted as shown in FIG. 6, then when applying the blood-glucose algorithm to the reference transient an error condition would be caused to occur in the algorithm, and the reference test result at step 28 would be erroneous. At step 29, processor 18 checks the meter reading against a predetermined range of acceptable readings (e.g. stored in memory storage 16b). If the reading is determined to be erroneous then at step 30 an error message may be displayed on display 18, indicating to the user that there is a meter problem and, for example, an instruction that they should contact the manufacturer of the meter.

If memory storage 16b is not corrupted, and if following application of the blood-glucose algorithm to the reference transient a narrow expected range (approximately ±0.2 mmol/L) of glucose concentration is determined, then meter-strip system 10 has been successfully tested, and no error message appears. The user may then proceed to use meter 12 to carry out blood-glucose measurements (or other test fluid measurements), knowing that the blood-glucose algorithm is not corrupted and the meter is functioning properly.

In some cases, the blood-glucose algorithm may be stored in some other memory of meter 12, but the algorithm code space or coefficient space may have been corrupted. If so, then even if the control solution transient is not contaminated with noise (as in FIG. 3) and memory storage 16b is intact such that the reference transient does not contain any anomalies (as in FIG. 4), erratic behaviour may nonetheless cause the system to crash (due to the corruption of the algorithm). This would clearly indicate to the user a problem with the meter. Even if the meter does not crash, in all likelihood the algorithm output would be very unusual and well outside the expected range, and the meter would display an error message which could be reported to the manufacturer.

Whilst specific embodiments have been described, it is to be understood that the contemplated embodiments are not limited to these embodiments, and that alterations, modifications, and variations of these embodiments may be carried out by the skilled person without departing from the scope of the claims. For instance, whilst described primarily in the context of verifying operation of a meter for reading electrochemical test devices, with particular reference to medical devices for measuring glucose in people with diabetes, the concepts embodied herein may equally well be used in other fields, for example in health and fitness, food, drink, bio-security applications, environmental sample monitoring, veterinary devices, etc.

Furthermore, whilst primarily described in the context of use with electrochemical test strips, the concepts embodied herein may extend to other electrochemical devices, such as wearable devices that actively acquire a fluid sample (such as interstitial fluid) from a user and cause an electrochemical reaction to occur with the sample. Examples of such are continuous (or semi-continuous) glucose monitoring devices used for controlling glucose concentrations (and insulin dosing) by users with diabetes.

The invention claimed is:

1. A method of verifying operation of a meter for reading electrochemical test devices, comprising:
   obtaining a reference transient indicative of a current vs time response generated at an electrochemical test device when the electrochemical test device reacts with a reference test fluid, wherein the reference test fluid is a bodily fluid sample and a non-control fluid, and wherein the electrochemical test device comprises at least one working electrode;
   applying with the meter an algorithm to the reference transient so as to obtain a reference test result, wherein the algorithm is for use in estimating an unknown concentration of an analyte in a sample of the reference test fluid; and
   determining whether the reference test result is valid on the basis of a predetermined range of acceptable readings so as to verify operation of the meter, further comprising storing the reference transient in a memory of the meter.

2. The method of claim 1, further comprising identifying an anomaly in the reference transient in response to determining the reference test result is not valid.

3. The method of claim 1, further comprising identifying an error in the algorithm in response to determining the reference test result is not valid.

4. The method of claim 1, further comprising determining a corruption of a memory of the meter, the memory storing the reference transient and/or the algorithm.

5. The method of claim 1, wherein the bodily fluid sample of the reference test fluid is any one of: blood, plasma, urine, saliva, lacrimal fluid, sweat, and interstitial fluid; or breath condensate.

6. The method of claim 1, wherein the reference transient is obtained from multiple transients generated using respective samples of the reference test fluid, each sample obtained from a member of a common demographic.

7. The method of claim 6, wherein the common demographic comprises any of the following: diabetics, non-diabetics, males, females, adults, and children.

8. The method of claim 1, wherein the reference transient is obtained from multiple transients generated using respective samples of the reference test fluid, each sample having substantially the same temperature.

9. The method of claim 1, wherein the analyte is one or more of: glucose, ketone, lactate, glycerol and cholesterol.

10. The method of claim 1, further comprising:
    applying a control fluid to an electrochemical test device;
    obtaining with the meter a control transient indicative of a response generated at the electrochemical test device when reacting with the control fluid; and
    verifying operation of the meter based on the control transient.

11. The method of claim 10, verifying operation of the meter based on the control transient comprises:
    using a current generated at the electrochemical test device when reacting with the control fluid to estimate a concentration of an analyte in the control fluid; and
    comparing the estimated concentration to a predetermined range of concentrations.

12. The method of claim 10, wherein the reference transient is pre-stored in the meter before applying the control fluid.

13. The method of any of claim 10, wherein the control fluid has a known concentration of the analyte.

14. A meter for reading electrochemical test devices, comprising:
    one or more memories storing:
      a reference transient indicative of a current vs time response generated at an electrochemical test device when the electrochemical test device reacts with a reference test fluid, wherein the reference test fluid is a bodily fluid sample and a non-control fluid, and wherein the electrochemical test device comprises at least one working electrode; and
      an algorithm for use in estimating an unknown concentration of an analyte in a sample of the reference test fluid; and
    a processor configured to:
      apply the algorithm to the reference transient so as to obtain a reference test result;
      determine whether the reference test result is valid on the basis of a predetermined range of acceptable readings so as to verify operation of the meter; and
      store the reference transient in a memory of the meter.

15. A non-transitory data carrier having a processor control code stored thereon, the processor control code configured, when read by a computer, to cause the computer to:
    obtain a reference transient indicative of a response generated at an electrochemical test device when the electrochemical test device reacts with a reference test fluid, wherein the reference test fluid is a bodily fluid sample and a non-control fluid, and wherein the electrochemical test device comprises at least one working electrode;
    apply with the meter an algorithm to the reference transient so as to obtain a reference test result, wherein the algorithm is for use in estimating an unknown concentration of an analyte in a sample of the reference test fluid;
    determine whether the reference test result is valid on the basis of a predetermined range of acceptable readings so as to verify operation of the meter; and
    store the reference transient in a memory of the meter.

* * * * *